United States Patent [19]

Cresswell et al.

[11] Patent Number: 5,218,211
[45] Date of Patent: Jun. 8, 1993

[54] SYSTEM FOR SAMPLING THE SIZES, GEOMETRICAL DISTRIBUTION, AND FREQUENCY OF SMALL PARTICLES ACCUMULATING ON A SOLID SURFACE

[75] Inventors: Michael W. Cresswell, Frederick; Richard A. Allen, Germantown; Loren W. Linholm, Ijamsville; Martin C. Peckerar, Silver Spring, all of Md.

[73] Assignee: The United States of America as represented by the Secretary of Commerce, Washington, D.C.

[21] Appl. No.: 781,615

[22] Filed: Oct. 23, 1991

[51] Int. Cl.⁵ ............................................. G01N 21/86
[52] U.S. Cl. ..................................... 250/571; 356/338
[58] Field of Search ...................... 250/571, 572, 222.2; 356/335, 336, 337, 338, 343

[56] References Cited

U.S. PATENT DOCUMENTS

| | | | |
|---|---|---|---|
| 4,377,340 | 3/1983 | Green et al. | 250/572 |
| 4,772,126 | 9/1988 | Allemand et al. | |
| 4,772,127 | 9/1988 | Chase et al. | 356/338 |
| 4,801,205 | 1/1989 | Tatsuno | |
| 4,895,446 | 1/1990 | Maldari et al. | |
| 5,076,692 | 12/1991 | Neukermans et al. | 356/338 |

OTHER PUBLICATIONS

"Auto Wafer Inspection: Tools for Your Process Problems", Semiconductor International, Dec. 1988.
"The Leading Edge Dynamic Particle Analysis" brochure on the Aerometrics Phase Doppler Particle Analyzer from Aerometrics, Inc., Sunnyvale, CA 94089.
"A Close Look into Particle Dynamics" brochure regarding the Particle Dynamics Analyzer from Dantec Elektronik.
"Integrate Analytical Techniques to Find Those Last Remaining Particles", Semiconductor International, May 1990.
"Process Equipment, Particularly the Process Tube, Is Chief Cause of Wafer Contamination", Semiconductor International, Mar. 1989.
"Process Plasmas Produce Particles", Semiconductor International, Dec. 1989.
"Development of a 2048×2048 Imager for Scientific Applications", J. C. Geary, Proceedings of SPIE—The International Society of Optical Engineering, vol. 1242, p. 38, Charge-Coupled Devices and Solid State Optical Senses, Feb. 12-14, 1990.
"Electrical Defect Monitoring for Process Control", Charles F. King, SPIE, vol. 1087 Integrated Circuit Metrology, Inspection, and Process Control III, 1989.

Primary Examiner—David C. Nelms
Attorney, Agent, or Firm—Michael M. deAngeli

[57] ABSTRACT

A system which samples and records the locations of opaque particles accumulating on a surface. The system represents graphically the geometrical distributions of the particles through an integral electronic hardware/-software subsystem. The key component is a radiant energy sensitive sensor which produces the sampling surface. The sensor is exposed to a constant level of radiant energy. Opaque particles becoming resident upon the sensor surface inhibit sensitization of the surface by the radiant energy and thereby indicates the presence and location of the particle. Embodiments of the sensor include charge coupled devices (CCDs), photodiode arrays, intrinsic or extrinsic "bulk" material, and optically- or UV-erasable memories.

30 Claims, 4 Drawing Sheets

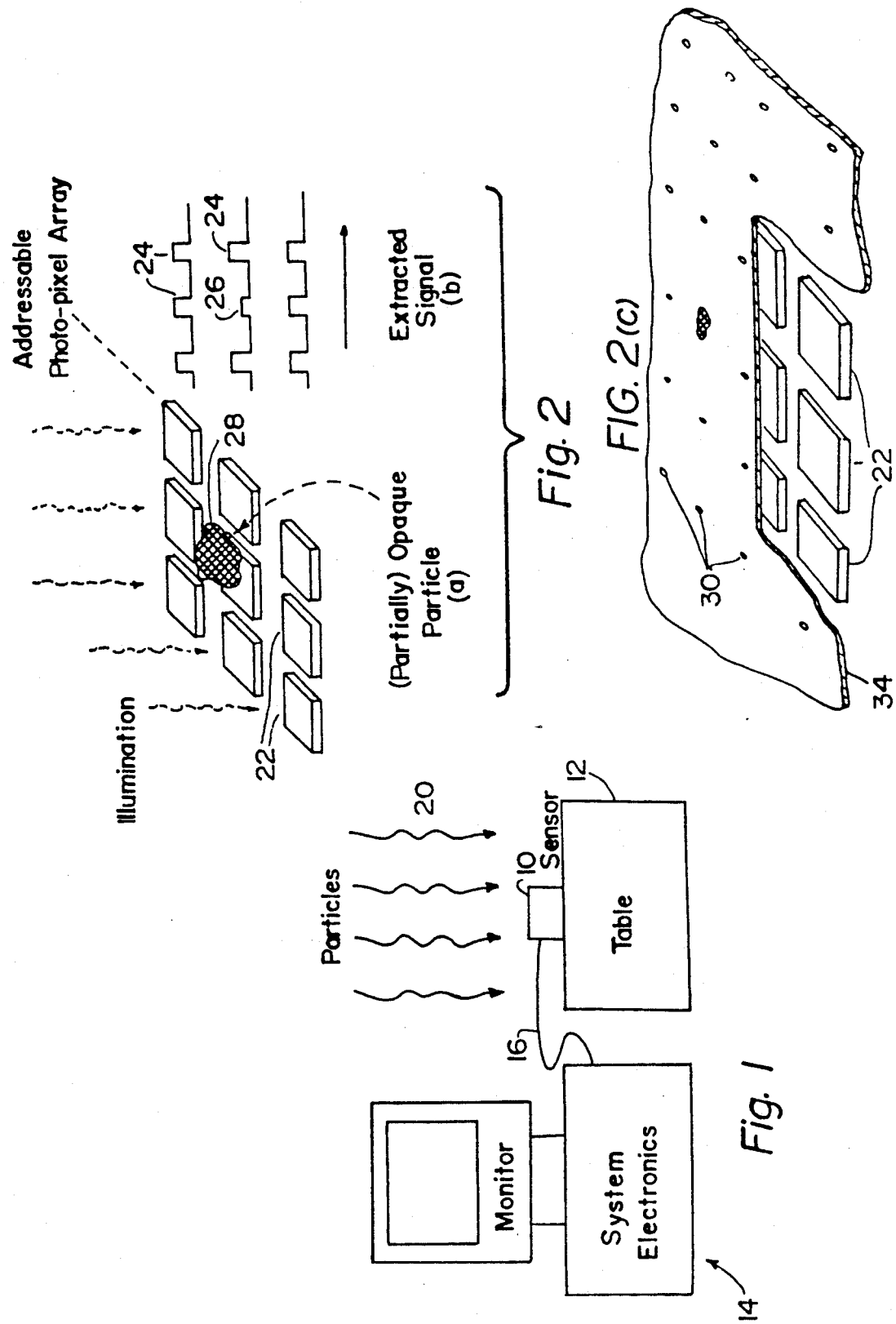

Two or more electrical continuity structures

SYSTEM FOR SAMPLING THE SIZES, GEOMETRICAL DISTRIBUTION, AND FREQUENCY OF SMALL PARTICLES ACCUMULATING ON A SOLID SURFACE

TECHNICAL FIELD

This invention relates to sampling systems, and more particularly to small particle sampling systems.

BACKGROUND ART

A need exists for an effective system for monitoring the prevalence of particles of dimensions of the order of one quarter micron. Possible applications include ultra large scale integration (ULSI); integrated circuit manufacturing and asbestos particle detection. Heretofore there has not been an economically feasible alternative way for reliably detecting and characterizing particulate contamination. Further, there has been no method for detecting and characterizing particulate contamination in compressed gasses or high pressure gas systems.

Those concerned with these and other problems recognize the need for an improved small particle sampling system.

DISCLOSURE OF THE INVENTION

The present invention provides a system which samples and records the locations of opaque particles accumulating on a surface. The system represents graphically the geometrical distributions of the particles through an integral electronic hardware/software subsystem. The key component is a radiant energy sensitive sensor which produces the sampling surface. The sensor is exposed to radiant energy. Opaque particles becoming resident upon the sensor surface limit the radiant energy incident thereon. Measurement of the energy allows determination of the presence and location of the particle. Further information about the size and composition of the particle can be determined by varying the intensity and output spectrum of the radiant energy. Embodiments of the sensor include charge coupled devices (CCDs), photodiode arrays, intrinsic or extrinsic "bulk" material, and optically-or UV-erasable memories.

An alternate system is a passive embodiment of this invention: a sample coated with photoresist is placed in the ambient to allow the settling of particles on the surface for a fixed amount of time. It is then patterned and processed. Any opaque particles on the order of, or larger than, the minimum feature size can be identified by their effects on the characteristics of the pattern.

An object of the present invention is the provision of an improved small particle sampling system.

Another object is to provide a small particle sampling system for reliably detecting and measuring particulate contamination.

BRIEF DESCRIPTION OF THE DRAWINGS

These and other attributes of the invention will become more clear upon a thorough study of the following description of the best mode for carrying out the invention, particularly when reviewed in conjunction with the drawings, wherein:

FIG. 1 is a schematic illustration of the present invention comprising a system which samples and records in real time the locations of opaque particles accumulating on solid surfaces;

FIG. 2(a) is a schematic illustration of the sensor consisting of an array of individually addressable photosensitive pixel cells exposed to radiant energy;

FIG. 2(b) illustrates typical signals provided by the rows of pixel cells of FIG. 2(a);

FIG. 2(c) shows a shutter over the sensor of FIG. 2(a);

BEST MODE FOR CARRYING OUT THE INVENTION

Figure 3:
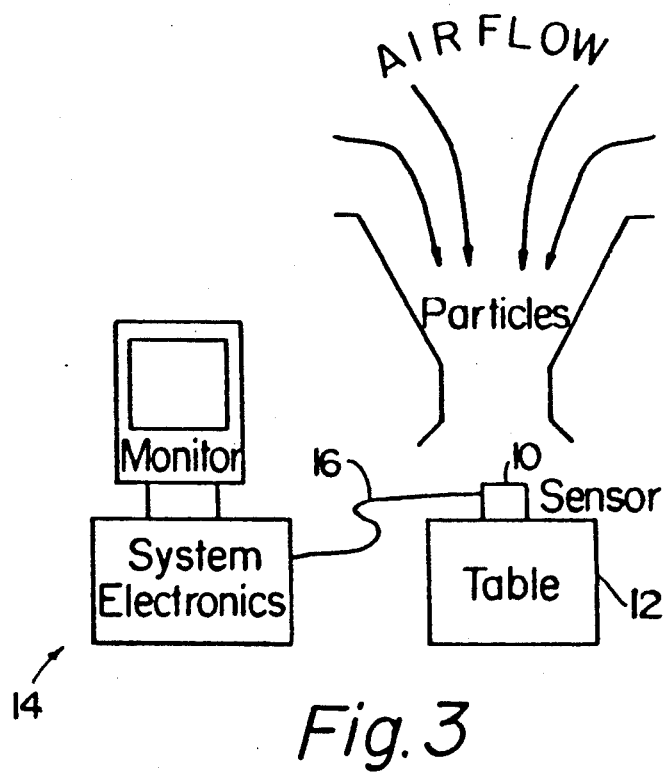
FIG. 3 is a schematic illustration of an embodiment where baffles are arranged to force the flow of ambient air or fluid over the sensor to enhance its particulate collection efficiency.

The best mode embodiment of the invention is a system which samples and records in real time the locations of opaque particles accumulating on a solid surface. The primary application of the invention is monitoring the prevalence of particles of dimensions of the order of one quarter micron in integrated circuit manufacturing facilities. This function is of significant and growing commercial importance since such particles are known to compromise the yield of manufacturing high density integrated circuits.

The presence of such particles thus increases the cost of manufacture of such circuits. Detection and characterization of the particles is a first step in their elimination.

The key component of the system is a sensor which provides a sampling surface. Described in this disclosure are several embodiments of the sensor. Each of these may be fabricated using highly advanced but generally proven semiconductor wafer processing technologies. The sensor itself consists of an array of scaled, individually-addressable, photo-sensitive pixel cells, optionally with integrated row-column decoding or other drive circuitry, for providing a video signal or the like. The array is exposed to radiant energy. When an opaque particle become resident on the sensor surface, a degraded signal is extracted from the corresponding pixel cell, thereby indicating the presence of the particle. Measurement of the amplitude of the video sign and of the difference in video signal in response to variation in the intensity and spectral output of the radiant energy source allows the determination of the size and, in some cases, the composition of the particle. A key enhancement of the sensor is shuttering the active, or sensitive, area of each pixel cell to improve the signal-to-noise ratio, allow the detection of smaller particles, and provide a more accurate measure as to particle size.

The sampling system represents graphically the geometrical distributions of the particles through an integral electronic hardware/software subsystem. The key component is a sensor 10 which provides the sampling surface. The sensor may be attached to the electronic subsystem 14 by a flexible cable 16 as illustrated in FIG. 1. Typically, the sensor may be placed on a solid surface 12 in a laboratory or on the inside wall of a vessel containing a liquid, gas, vapor, vacuum, or plasma. As opaque airborne particulates 20, or contaminants from other sources, become incident on the active surface of the sensor, they are detected and their locations are represented on an image generated by the electronic subsystem 18. The system has embedded software that presents the geometrical distribution of particle sizes that may have become resident on the sensor's active surface during any particular sampling period specified by an operator. The system may also have a knowledge-based expert system or neural net software that assists the operator to make a determination of the nature and/or source of the contaminant patterns being observed.

To improve the efficiency of any of the embodiments of this system, the system can be designed so the sensor examines large volumes of ambient air of fluid as shown in FIG. 3.

The key component of the system is the sensor 10. One embodiment of the sensor consists of an array of individually addressable photo-sensitive pixel cells 22, optionally with integrated row-column decoding or other drive circuitry. The array is illuminated with a constant level of illumination as shown in FIG. 2. A full signal is normally extracted from each pixel cell, as indicated by pulses 24 in FIG. 2(b). However, if an opaque particle 28 become resident on sensor surface, a degraded video signal (see pulse 26) will be extracted from the underlying pixel cell thereby indicating the presence of the particle.

There is a range of options for implementing a semiconductor-based integrated cell array for the sensor. Among these implementation options are photodiode arrays, intrinsic or extrinsic "bulk" material, CCDs (Charge Coupled Devices), or optically-erasable memories. Applicants presently believe that, relative to the state of the art of all these, CCD arrays are probably the most suitable for implementation at this time.

Charge coupled devices are analog shift registers in which a sequence of charge packets are contained and shifted simultaneously within potential wells along the surface of a silicon chip by applying clock voltages to overlying insulated gate electrodes. A CCD used as an image sensor stores charge packets responsive to the intensity of light incident on each of a large array of pixel cell surfaces. Usually an output electrode connected to an on-chip integrated amplifier reads the sizes of sequential charge packets. A video signal may be generated responsive to the read-out values of the sequence of charge packets. Among factors determining the performance of a CCD used as an electronic image sensing and read-out device are its resolution, the quantum efficiency of its photorecorders, and the signal-to-noise ratio of its output signal.

The CCD cell has been scaled to smaller areas since the technology was developed. Throughout this process, the absolute size of the collection area of the cell has remained substantially larger than the minimum feature size, due to the primary applications of CCDs such as still photography (to allow measurement of extremely low intensity sources) and video cameras (to increase bandwidth). Due to the large sizes of the cells and a noise margin of about $10^4$, present state-of-the art would be marginal at discerning single particles at the minimum feature size. That is, the sensitized areas or pixel cells of the CCD sensors re much larger than the dimensions of conductors to be formed on IC chips. Therefore a particle might be sufficiently large to interfere with formation of such a small feature, but would not obscure a substantial portion of one of the active pixel cell surfaces of the CCD, making detection of the particle by measuring the CCD's output signal difficult. However, there is no apparent technical reason the cells of the CCD could not be scaled such that a single particle at about the minimum feature size could cause subtraction of up to 0.25% of the full-on signal; such a change is easily detectable with state-of-the-art optical imaging CCD technology.

An enhancement of the sensor which avoids the requirement of scaling is shuttering the active, or sensitive, area of each pixel, cell, reducing the active area of each pixel cell. Shuttering 34 can be provided by aligning the pixel cells with at least one aperture in otherwise opaque gate films. See FIG. 2(c). Such apertures might be made smaller than minimum feature sizes through the use of focused ion beam etching or some other high precision technique. The net effect is to reduce the optically sensitive active area of the CCD cell, and hence to increase its signal to noise ratio with respect to small particles. For example, to detect reliably particles on the order of 0.1 $\mu$ radius, comparable to line widths of 0.2 $\mu$ as now contemplated, the apertures in the opaque shutter should be on the order of 0.1 $\mu$ radius. The ratio of the areas of the one or more apertures over each pixel cells to the areas of the corresponding light-sensitive pixel cell surfaces of the CCD (typically 20 $\mu \times 20$ $\mu$, or 400 $\mu^2$) may thus be up to on the order of 1:1000.

Applicants intend that the technique disclosed here covers the other implementations of the concept mentioned. In particular, an array of cells each having one of the devices that is used to sense optically generated charge after it has been collected from a CCD channel, together with a very short channel CCD, could be addressed by a random access technique. A large area array of such cells could be checked for the presence of a particle's shadow at high repetition rates.

An alternative device technology with which to fabricate the sensor is that used to manufacture radiant energy-erasable (including both optical and ultra violet (UV) erasable) programmable read-only memories. In operation, a map of particle locations would be registered through reading the locations of cells that retained polarity during optical erasure. Another related implementation that would maximize the advantage of existing technology is a modified dynamic would be ensuring that the cell control switching transistor is photosensitive. In this embodiment, the photo-sensitive areas of the transistors would define the active pixel cells. If the DRAM were loaded with ones on a write cycle, the presence of particles shielding the transistor would be registered by readable cell memory retention. Unshielded cells would discharge providing a change in polarity that would be observed on the next read cycle. The photosensitive device could alternatively be a photodiode connected across each cell's storage capacitor. This could make such an implementation of the solid state particle sensor very attractive by virtue of its sensitivity to very small particles. Either supplementary implementation disclosed here could benefit from the perforated metal shielding film 34 disclosed therein.

ALTERNATE EMBODIMENTS OF THE INVENTION

Active DC Test Structure Approach

Figure 4:
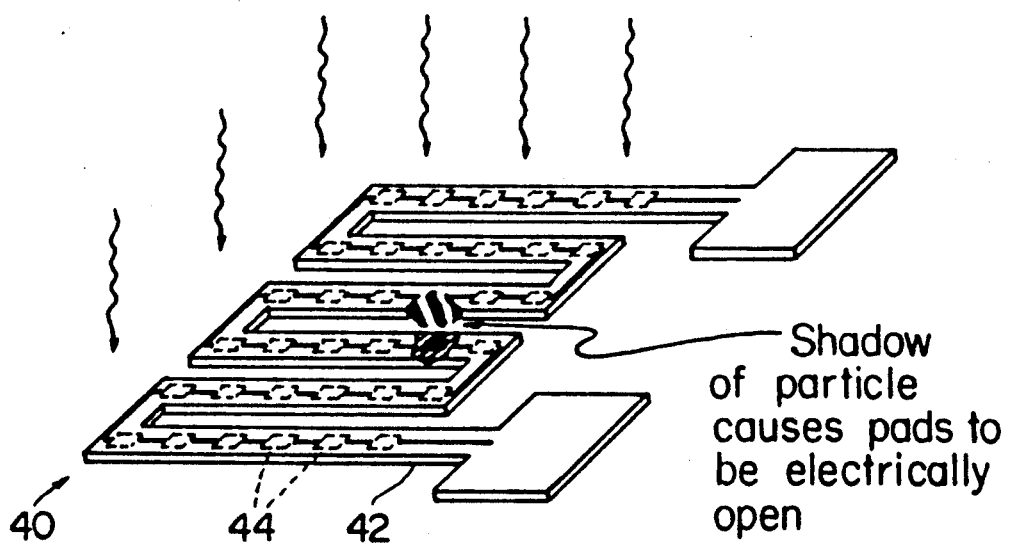
FIG. 4 is a schematic illustration of an embodiment where a particle shadow sensor is a serpentine with sections of photoconductive material or photo-sensitive devices, or both, electrically connected in series.

Consider a two-terminal device 40 consisting of an electrical continuity test structure 42, which is maximize active area can be made in serpentine form, embedded in an insulating material together constituting the sensor sampling plane. Sections 44 of the serpentine conductor are made from a photoconductive material or a string of photo-sensitive devices or both, electrically connected in series, as suggested in FIG. 4. The device exhibits nominal electrical conductivity from terminal to terminal only when all the photoconducting sections are illuminated. If the sensor plane is illuminated and the space between the source of illumination and the serpentine contains an opaque particle, the particle will project a shadow onto the serpentine. The presence of an opaque particle will be detected as a diminution of, or break in, the electrical continuity of the serpentine as a consequence of the shadow. The principle may be applied either to a static air sample or to a moving air stream or its particles resident on the surface accommodating the sensor. The concept could be implemented either with or without the perforated opaque shield 34 described above for the preferred embodiment described in the prior section.

Figure 8:
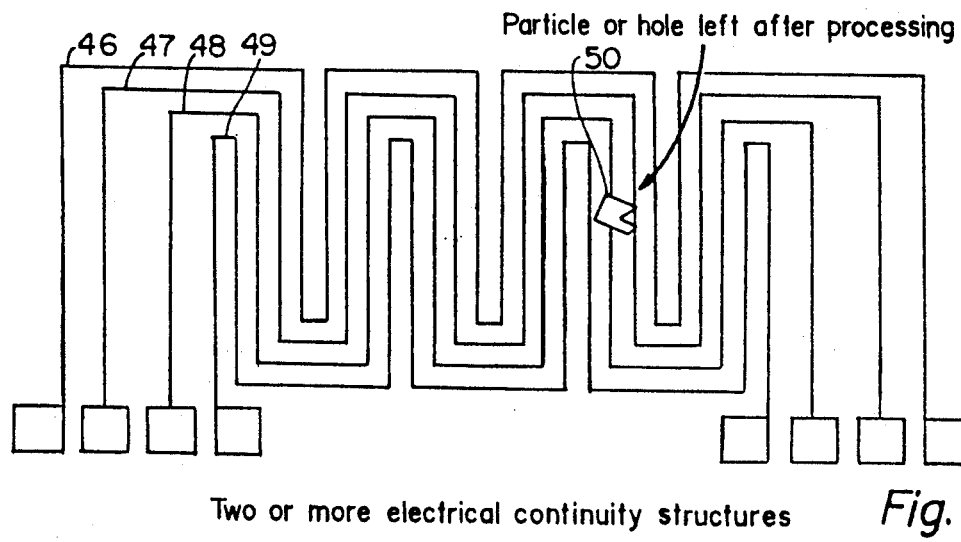
FIG. 8 is a schematic illustration of an embodiment where the particle sensor includes multiple parallel two-terminal serpentines. These serpentines are either of the type shown in FIG. 4 or FIG. 7.

An enhancement to this embodiment is to use multiple, parallel serpentine conductors 46–49 at a known separation (such as is shown in FIG. 8). A particle 50 resident on this surface will cause a diminution of, or break in the electrical continuity of one or more of the serpentines. Based on the number of serpentine conductors whose electrical connectivity is affected, the dimensions of the particle can be inferred.

Passive Off-Line Particulate Sampling

Figure 5A:
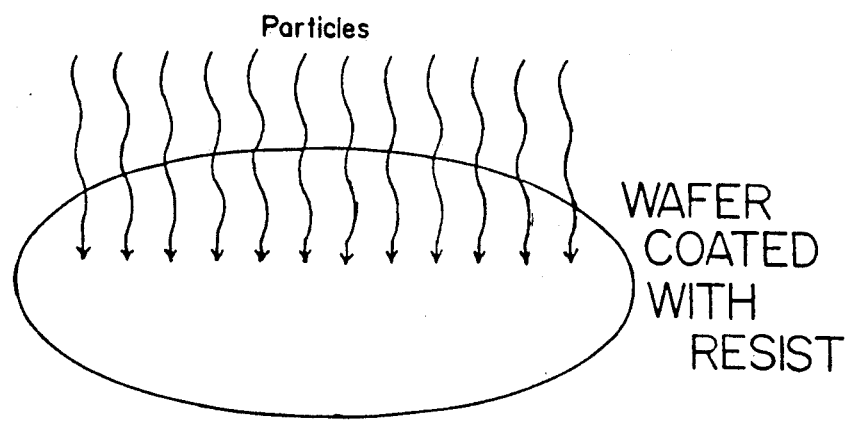
FIG. 5(a) and 5b are is a schematic illustration of passive embodiment of the present invention. A wafer which has been coated with photoresist is placed in the ambient of air or fluid to allow the collection of particles on its surface. It is then patterned with electrical continuity test designs and processed. The presence of particles is determined by comparing observed continuity; with expected continuity.
Figure 5B:
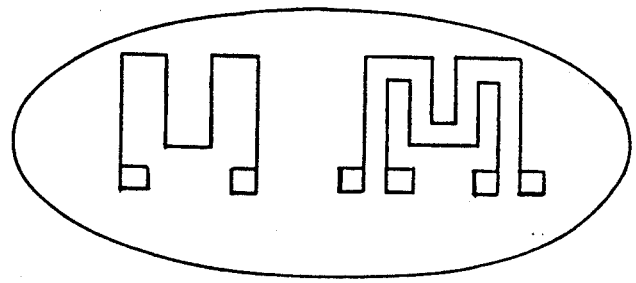
Figure 7:
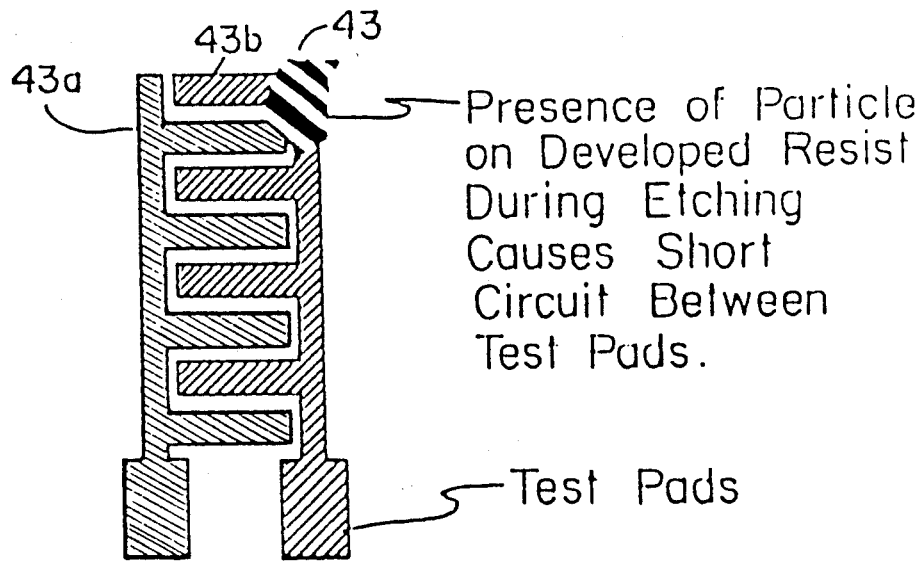
FIG. 7 is a schematic illustration of an embodiment where the particle sensor includes a two-terminal conducting serpentine defined in negative resist, wherein the resist remains soluble where shadowed by a particle and the presence of the particle is detected as an "open" in what was selectively exposed as a continuous path.

The passive sensor is an insulating substrate on which a conducting film is deposited. The conducting film is further coated with photoresist. See FIG. 5(a). After the sensor has been placed in the environment being sampled, it is processed through an automatic particle density extraction system. In this system, the substrate is exposed to a source of radiation (optionally with characteristics identical/similar to that being used for IC device manufacture) through a mask patterned with electrically testable defect monitors. The resist is developed and the system selectively removes metal to provide the testable patter. See FIG. 5(b). Electrical testing is thus performed to extract the presence of defects of various sizes. These defect densities are converted to airborne particle densities by calibration curves embedded in the system's computer and delivered to the operator.

Figure 6:
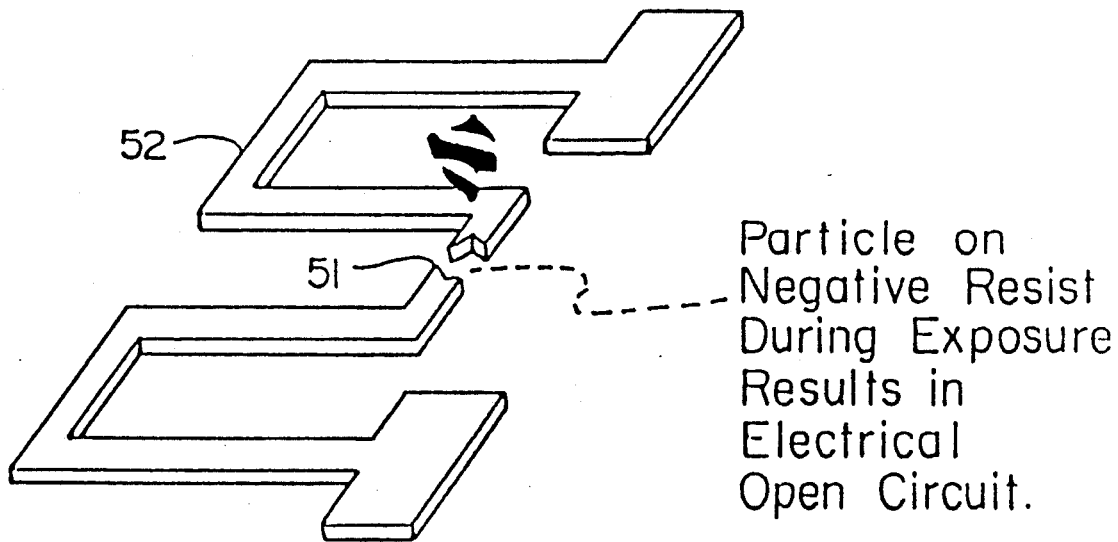
FIG. 6 is a schematic illustration of an embodiment where the particle sensor includes a positive resist over a conducting film patterned with an intra-level isolation test structure, wherein opaque particles cause underlying residual metal to short drawn isolation segments after pattern replication by etching.

One specific implementation features positive resist which is rendered soluble in developer by radiation during exposure. The presence of opaque particles on the resist prior to and during exposure results in residual metal 43 that serves as a short circuit between nominally isolated segments 45a, 45b of the test structure as shown in FIG. 5. Alternatively, in another specific implementation, a two-terminal serpentine conductor is imaged in negative resist. The resist remains soluble wherever it is shadowed by a particle. The presence of a particle would be detected as on "open" 51 in a continuous conducting path 52 as illustrated in FIG. 6. An enhancement of this technique is to use multiple, parallel serpentines, as in FIG. 8. Based on the number of serpentines which are "open", the size of the particle can be inferred.

Both the positive and negative resist test patterns described above could be used to monitor particulate contamination that shields material from plasma etching. For example, if an isolation pattern has been developed in the resist on a substrate, and the substrate has since been exposed to particulate contamination that shadows the metal etch, then the presence of these etch-impervious particles will be identified as shorts between drawn isolated segments.

Finally, hybrids of the above techniques may prove applicable to particular situations. For example, particles whose presence is manifested in residual areas of opaque films, as described in FIG. 5, can be recorded by a sensor of the type shown in FIG. 2. In this case, the metal film in which the presence of particles if recorded is deposited over the array shown in FIG. 2.

All the off-line sensors described above feature multiple-design rule geometries to enable extraction of effective particle size distributions. That is, preferably the conductive patterns formed on the sensor surfaces exhibit features of varying size, to enable discrimination between particles of various sizes.

Obviously, many modifications and variations of the present invention are possible in light of the above teachings. It is therefore to be understood that, within the scope of the appended claims, the invention may be practiced otherwise than as specifically described.

We claim:

1. Apparatus for detecting the presence of particles on a sampling surface, comprising:
   a source of illuminating radiation disposed to illuminate sampling surface, comprising:
   a sensor comprising a plurality of pixel cells sensitive to said illuminating radiation, said sampling surface including said pixel cells, each said pixel cell providing an output signal responsive to the intensity of said illuminating radiation thereof;
   means for determining the relative intensity of illuminating radiation on each pixel cell responsive to the output signal provided by each of said pixel cells; and
   means for determining the presence of particles on said pixel cells responsive to comparison of the relation intensity of the illuminating radiation thereon.

2. The apparatus of claim 1, further comprising shutter means for preventing illuminating radiation from being incident on portions of said pixel cells.

3. The apparatus of claim 2, further comprising means for determining the relative sizes and distribution of said particles.

4. The apparatus of claim 2, wherein said shutter means comprises a member opaque to said illuminating radiation disposed between said source of illuminating radiation and said sampling surface, said member having apertures of predetermined size extending therethrough in registration with said pixel cells.

5. The apparatus of claim 4, wherein at least one of said apertures are provided in said opaque member in registration with each said pixel cell.

6. The apparatus of claim 1, wherein said pixel cells are comprised by a radiation sensitive charge coupled device (CCD).

7. The apparatus of claim 1 further comprising means for varying the intensity and output spectrum of said illuminating radiation.

8. The sampling system of claim 1 wherein each pixel cell comprises a radiant energy-erasable memory cell.

9. The sampling system of claim 1 wherein the sensor is a UV-erasable programmable read-only memory.

10. The sampling system of claim 8 wherein the geometrical distribution of the particles is registered through reading the locations of the cells that retain polarity during radiant energy exposure.

11. The sampling system of claim 9 wherein the geometrical distribution of the particles is registered through reading the locations of the cells that retain polarity during UV exposure.

12. The sampling system of claim 1 wherein the sensor is a multiple-cell DRAM-type memory device wherein each cell includes a photo-sensitive control switching transistor.

13. The sampling system of claim 1 wherein the sensor is a multiple-cell DRAM-type memory device wherein each cell includes a storage capacitor and a photodiode across the storage capacitor.

14. A small particle sampling system, comprising:
sensor means for sensing radiant energy, the sensor means forming a sampling surface for receiving particles;
means for exposing the sensor means to radiant energy;
means for measuring variations in the sensitization of the sampling surface by the radiant energy; and
means for determining the sizes, geometrical distribution and frequency of the particles resident on the sensor means based on the measured spectral and geometrical variations in the sensitization of the sampling surface,
wherein said sensor means is a two-terminal device having an electrically continuity test structure embedded in an insulating material, wherein sections of the electrical continuity test structure are made of photoconductive material.

15. The sampling system of claim 14 wherein the electrical continuity test structure is laid out in a serpentine fashion.

16. A small particle sampling system, comprising:
sensor means for sensing radiant energy, the sensor means forming a sampling surface for receiving particles;
means for exposing the sensor means to radiant energy;
means for measuring variations in the sensitization of the sampling surface by the radiant energy; and
means for determining the sizes, geometrical distribution and frequency of the particles resident on the sensor means based on the measured spectral and geometrical variations in the sensitization of the sampling surface;
wherein the sensor is a set of parallel, two-terminal devices separated at a known distance, having electrical continuity test structures embedded in a insulating material, wherein sections of the electrical continuity test structures are made of photoconductive material.

17. The sampling system of claim 16 wherein the electrical continuity test structure are laid out in a serpentine fashion.

18. A small particle sampling system, comprising:
sensor means for sensing radiant energy, the sensor means forming a sampling surface for receiving particles;
means for exposing the sensor means to radiant energy;
means for measuring variations in the sensitization of the sampling surface by the radiant energy; and
means for determining the sizes, geometrical distribution and frequency of the particles resident on the sensor means based on the measured spectral and geometrical variations in the sensitization of the sampling surface, wherein the sensor means is a two-terminal device having an electrical continuity test structure embedded in an insulating material, wherein sections of the electrical continuity test structures are made of a string of photo-sensitive devices electrically connected in series.

19. The sampling system of claim 18 wherein the electrical continuity test structure is laid out in a serpentine fashion.

20. A small particle sampling system, comprising:
sensor means for sensing radiant energy, the sensor means forming a sampling surface for receiving particles;
means for exposing the sensor means to radiant energy;
means for measuring variations in the sensitization of the sampling surface by the radiant energy; and
means for determining the sizes, geometrical distribution and frequency of the particles resident on the sensor means based on the measured spectral and geometrical variations in the sensitization of the sampling surface, wherein the sensor means is a set of parallel, two-terminal devices separated at a known distance, having electrical continuity test structures embedded in an insulating material, wherein sections of the electrical continuity test structures are made of a string of photo-sensitive devices electrically connected in series.

21. The sampling system of claim 20 wherein the electrical continuity test structure are laid out in a serpentine fashion.

22. A method for detecting the presence of particles on a sampling surface, comprising the steps of:
(i) illuminating said sampling surface with illuminating radiation, said sampling surface comprising a plurality of pixel cells each sensitive to said illuminating radiation, each said pixel cell providing an output signal responsive to the intensity of said illuminating radiation thereon;
(ii) determining the relative intensity of the radiation incident on said pixel cells responsive to the output signals provided by each of said pixel cells; and
(iii) determining the presence of particles on said sampling surface responsive to comparison of the relative intensities of radiation incident on said pixel cells.

23. The method of claim 22, comprising the further step of determining the relative sizes and distribution of said particles.

24. The method of claim 23, comprising the further steps of disposing means opaque to said illuminating radiation between said source of illuminating radiation and said sampling surface, said means having apertures of predetermined size extending therethrough in registration with said pixel cells, and calculating the determined relative sizes and distributions of said particles responsive to the predetermined size of said apertures with respect to the size of said pixel cells.

25. The method of claim 24, wherein one or more said aperture are provided in registration with each of said pixel cells.

26. The method of claim 22, comprising the further step of varying the intensity and output spectrum of said illuminating radiation.

27. The method of claim 22, comprising the further steps of:
(a) characterizing the responses of said pixel cells to particular illuminating radiation upon manufacture of an instrument comprising said sampling surface;
(b) exposing said instrument to ambient conditions wherein the presence of particles is to be detected;
(c) performing said steps (i) and (ii); and
(d) determining the presence of particles on said sampling surface by comparison of the output signals provided by each of the sensors to the response of said pixel cells in said characterization step (a).

28. A method for detecting and measuring particles on a surface, comprising the steps of:
determining a sequence of integrated-circuit fabrication steps which when performed with respect to a predetermined integrated circuit instrument design in the absence of such particles will yield conductive paths of predetermined characteristics on said surface;
performing said sequence of steps with respect to an example of said instrument design, while exposing the example to ambient conditions to be monitored for the presence of such particles at one or more points in said sequence; and
examining the characteristics of said conductive paths at completion of said sequence to determine whether particles interfered with the performance of said steps.

29. The method of claim 28, wherein said paths are of serpentine form.

30. The method of claim 28, wherein the dimensions of said paths are comparable to the minimum dimensions of said particles to be detected.

* * * * *